United States Patent [19]

Jackson

[11] Patent Number: 4,861,756
[45] Date of Patent: Aug. 29, 1989

[54] SYNTHETIC PULMONARY SURFACTANT

[75] Inventor: Richard L. Jackson, Cincinnati, Ohio

[73] Assignee: Merrell Dow Pharmaceuticals Inc., Cincinnati, Ohio

[21] Appl. No.: 266,263

[22] Filed: Oct. 26, 1988

Related U.S. Application Data

[63] Continuation of Ser. No. 169,092, Mar. 8, 1988, abandoned, which is a continuation of Ser. No. 88,031, Aug. 18, 1987, abandoned, which is a continuation of Ser. No. 801,172, Nov. 22, 1985, abandoned.

[51] Int. Cl.$^4$ .................... A61K 37/02; C07K 7/08; C07K 7/10
[52] U.S. Cl. ........................ 514/11; 514/13; 530/324; 530/325; 530/326
[58] Field of Search ............... 514/11, 13; 530/324, 530/325, 326

[56] References Cited

U.S. PATENT DOCUMENTS

| 4,312,860 | 1/1982 | Clements | 514/78 |
| 4,338,301 | 7/1982 | Tetsuro et al. | 424/95 |

FOREIGN PATENT DOCUMENTS

| 55041 | 6/1982 | European Pat. Off. |
| 77752 | 4/1983 | European Pat. Off. |
| 145005 | 12/1983 | European Pat. Off. |
| 110498 | 6/1984 | European Pat. Off. |
| 119056 | 9/1984 | European Pat. Off. |
| 3229179 | 5/1982 | Fed. Rep. of Germany |
| 3445226 | 8/1985 | Fed. Rep. of Germany |
| 56-110615 | 9/1981 | Japan |
| 58-164513 | 3/1982 | Japan |
| 58-183620 | 4/1982 | Japan |
| 59183621 | 4/1982 | Japan |
| 58-222022 | 6/1982 | Japan |
| 6034905 | 8/1983 | Japan |
| 59-76016 | 4/1984 | Japan |
| 2082457 | 3/1982 | United Kingdom |

OTHER PUBLICATIONS

R. T. White et al., *Nature*, 317(26), 361 (1985).
A. Argiolas and J. J. Pisano, *J. Biol. Chem.*, 260(3), 1437 (1985).
Chaffee and Greisheimer, *Basic Physiology and Anatomy*, J. P. Lippincott Co., New York, 1974, pp. 358-361.
J. B. West, ed., *Physiological Basis of Medical Practice*, 11th ed., Williams and Wilkins, Baltimore, 1985, pp. 586-592.

*Primary Examiner*—Delbert R. Phillips
*Attorney, Agent, or Firm*—Stephen L. Nesbitt

[57] ABSTRACT

Certain polypeptide-phospholipid complexes consisting of the amphipathic, helical portion of human apo A and its analogs and a phospholipid are useful in the treatment of neonatal respiratory distress syndrome.

23 Claims, No Drawings

SYNTHETIC PULMONARY SURFACTANT

CROSS-REFERENCE TO RELATED APPLICATION

This is a continuation of application Ser. No. 169,092, filed Mar. 8, 1988, which is a continuation of application Ser. No. 088,031, filed Aug. 18, 1987, now abandoned, which is a continuation of application Ser. No. 801,172, filed Nov. 22, 1985, all now abandoned.

BACKGROUND OF THE INVENTION

Respiratory distress syndrome (RDS) is the leading cause of death in prematurely born infants. It is estimated that over 25,000 deaths occur each year in the United States due to RDS. Neonatal RDS results from the inability of the lungs of premature infants to produce pulmonary surfactant. This surfactant is normally secreted by the type 2 alveoli cells of the lung and coats the alveolar lining. This coating acts to lower the surface tension at the air-liquid interface and greatly facilitates alveoli expansion upon inhalation thereby preventing collapse of air sacs on expiration. The lungs of infants lacking pulmonary surfactant are stiff, difficult to inflate, partially collapsed and fluid filled. Infants suffering from RDS become cyanotic and hypoxic.

While the precise composition of pulmonary surfactant is still uncertain, it is believed to be a complex of dipalmitoyl phosphatidylcholine (DPPC), a phospholipid, and apoprotein A (apo A), one of the two major protein components of the lung. The human apo A gene was recently isolated and its nucleotide sequence characterized by White et al., *Nature*, 317(26), 361 (1985). As a result, the amino acid sequence of apo A can, largely, be deduced.

Currently, neonatal RDS therapy is supportive in nature, directed toward assisting essential bodily functions and minimizing secondary complications until the newborn is able to breathe normally without assistance. In some severe cases, continuous positive airway pressure is effective by preventing lung collapse and by providing an oxygen enriched air supply. Although effective, such treatment presents risks of air leaks which can lead to interstitial pulmonary emphysema, pneumomediastinum and tension pneumothorax and can only be used where infant intensive care is available.

More recently, surfactant isolated by alveolar wash of sheep, Tween (fatty acid esters of polyethylene oxide sorbitan), and human surfactant have been shown to be effective when administered to human infants suffering from RDS and in animal failing lung models. The use of natural surfactant from animals and humans in the treatment of RDS, is however limited by the lack of its ready availability and the variability of the effectiveness of natural surfactant from batch to batch.

Applicant has discovered polypeptide-phospholipid complexes which consist of the amphipathic, helical portion of human apo A and certain of its analogs and a phospholipid such as DPPC. These complexes when administered to infants suffering from RDS act as a substitute for natural pulmonary surfactant.

SUMMARY OF THE INVENTION

Polypeptide-phospholipid complexes consisting of a polypetide of formula 1

$$T_N\text{-}A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12}$$
$$\text{-}A_{13}\text{-}A_{14}\text{-}A_{15}\text{-}A_{16}\text{-}A_{17}\text{-}A_{18}\text{-}A_{19}\text{-}A_{20}\text{-}A_{21}\text{-}T_C \quad 1$$

wherein $A_1$, $A_4$, $A_5$, $A_8$, $A_9$, $A_{11}$, $A_{12}$, $A_{15}$, $A_{16}$, $A_{18}$, $A_{19}$ and $A_{20}$ are each independently selected from Gln, Glu, Asp, His, Arg, Lys, Ser, Ala, Gly, Tyr, Typ, and Thr;

$A_2$ is Leu, Gln, Glu, Asp, His, Arg, Lys, Ser, Ala, Gly, Thr, Typ or Thr;

$A_3$ is Pro, Ile, Val, Phe, Met, Ala, Gly, Tyr, Typ or Thr;

$A_6$, $A_7$, $A_{13}$ and $A_{14}$ are each independently selected from Leu, Ile, Val, Phe, Met, Gln, Glu, Asp, His, Arg, Lys, Ser, Ala, Gly, Tyr, Typ and Thr;

$A_{10}$, $A_{17}$ and $A_{21}$ are each independently selected from Leu, Ile, Val, Phe, Met, Gln, Glu, Asp, His, Arg, Lys, Ser, Ala, Gly, Tyr, Typ, and Thr;

$T_N$ is
 $T_N'$-Arg-Gly-Pro-Pro,
 $T_N'$-Gly-Pro-Pro-,
 $T_N'$-Pro-Pro-,
 $T_N'$-Pro-, or
 $T_N'$-;

$T_C$ is
 -Leu-Gln-Thr-Arg-Gly-$T_C'$,
 -Leu-Gln-Thr-Arg-$T_C'$,
 -Leu-Gln-Thr-$T_C'$,
 -Leu-Gln-$T_C'$,
 -Leu-$T_C'$, or
 L -$T_C'$;

$T_N'$ is hydrogen, an amino acid, dipeptide, or tripeptide, or an aliphatic, aromatic or cyclic organic acid having from 1 to 10 carbon atoms; and $T_C'$ is hydrogen, a ($C_1$–$C_6$) alkyl, or benzyl optionally substituted with one or two members of the group consisting of nitro, methyl and methoxy, or $T_C'$ is phenacyl, phthalimidomethyl, benzhydryl, trichloroethyl, 4-picolyl, β-methylthioethyl or 4-(methylthio)-phenyl or a pharmaceutically acceptable salt thereof and a phospholipid act as pulmonary surfactants and are useful in the treatment of neonatal RDS.

DETAILED DESCRIPTION OF THE INVENTION

The following common abbreviations of the naturally occurring amino acid are used throughout this specification:

Gly—glycine
Ala—alanine
Val—valine
Leu—leucine
Ile—isoleucine
Pro—proline
Phe—phenylalanine
Trp—tryptophan
Met—methionine
Ser—serine
Thr—threonine
Cys—cysteine
Tyr—tyrosine
Asn—asparagine
Gln—glutamine
Asp—aspartic acid
Glu—glutamic acid
Lys—lysine Arg—arginine
His—histidine The natural amino acids, with the exception of glycine, contain a chiral carbon atom. Unless otherwise specifically indicated, the optically active amino acids, referred to herein, are of the L-configuration. As is customary, the structure of peptides written out herein is such that the amino terminal end is on the left side of the chain and the carboxy terminal end is on the right side of the chain.

The phospholipids of the protein-phospholipid complexes of this invention can be any phospholipid and this term as used herein includes the phosphoglycerides and the sphingolipids. Phosphoglycerides are those di-fatty acid esters of glycerol in which the remaining hydroxy group, a terminal hydroxy group, of the glycerol moiety forms an ester with phosphoric acid. Commonly the phosphoric acid moiety of the phosphoglycerides forms a second ester with an alcohol such as ethanolamine, serine, choline, or glycerol. Sphingolipids are those mono-fatty acid esters of sphingosine or dihydrosphingosine in which the hydroxy group at the 1- position forms an ester with the choline ester of phosphoric acid.

Suitable fatty acids for use in the phospholipids of this invention are those long chain carboxylic acids produced by both plants and animals, typically unbranched and containing an even number of carbon atoms. The fatty acids can be either saturated or unsaturated. The olefinic unsaturations are commonly of the "Z" configuration. Representative fatty acids are butyric, caproic, caprylic, capric, lauric, myristic, palmitic, stearic, arachidic, oleic, linoleic, γ-linolenic arachidonic and linolenic acids.

Preferably the fatty acid of the sphingolipids will be palmitic acid. Also preferred are those phosphoglycerides which contain two identical fatty acids. More preferably the phosphoglycerides will contain two palmitic acid residues. It is preferred that the phosphoric acid moiety of the phosphoglycerides form a second ester. More preferably the alcohol of this ester will be choline. The most preferred phospholipid of this invention is dipalmitoylphosphatidylcholine (DPPC) although polypeptidephospholipid complexes wherein the phospholipid consists of up to about one-third dipalmitoylphosphatidylglycerol (DPPG) are also preferred.

The formula 1 polypeptides of this invention are amphipathic peptides. Such peptides have the ability to complex with various amphipathic molecules including phospholipids by virtue of their unique helical structure wherein one outer area of the helix contains hydrophilic amino acid residues and another outer area contains hydrophobic amino acid residues. The hydrophilic area ($A_4$, $A_5$, $A_8$, $A_9$, $A_{11}$, $A_{12}$, $A_{15}$, $A_{16}$, $A_{18}$, $A_{19}$, $A_{20}$) has the ability to tightly complex the polar head groups of the phospholipids whereas the hydrophobic area ($A_6$, $A_{10}$, $A_{14}$ and $A_{17}$) complexes with the nonpolar, fatty acid groups of the phospholipids. Preferably the amino acid sequence in the formula 1 polypeptide will be the natural sequence of the amphipathic portion of the apo A protein with from one to five substitutions. Preferably the substitutions from the natural sequence will involve $A_1$, $A_2$, $A_3$, $A_4$, $A_5$, $A_{17}$, $A_{18}$, $A_{19}$, $A_{20}$, $A_{21}$, $A_7$ or $A_{13}$. More preferably the substitution will involve $A_7$ or $A_{13}$ which are Asp and Thr in the natural sequence. More preferably replacement of the natural amino acid at $A_7$ or $A_{13}$ will be with a hydrophobic amino acid such as Ile, Leu, Phe, Trp, Tyr or Val. Most preferably $A_7$ and $A_{13}$, when other than the natural amino acid residue will be Leu. It is also most preferred that the polypeptide of formula 1 will be the natural sequence of amino acids of the amphipathic portion of apo A and will be as follows:

$T_N$-Gly-Leu-Pro-Ala-His-Leu-Asp-Glu-Glu-Leu⎤
⎣Gln-Ala-Thr-Leu-His-Asp-Phe-Arg-His-Gln-Ile-$T_C$ wherein $T_N$ and $T_C$ are as defined above.

While the polypeptides of this invention contain, as drawn, twenty-one or more amino acids it is believed likely that polypeptides of formula 1 having from one to five amino acid residues less on the amino terminal and carbon terminal ends will also be effective so long as the polypeptide contains at least 14 amino acid residues. In a like manner one or more of the amino acids defined by $A_1$, $A_2$, $A_3$, $A_4$, $A_5$, $A_{17}$, $A_{18}$, $A_{19}$, $A_{20}$, $A_{21}$ can have the D configuration (if other t glycine) and any of the amino acids of the groups $T_N$ and $T_C$ can also have a D configuration. In particular, where $A_2$ is Leu, this Leu may be of the D-configuration. Moreover, any one or two of the amino acids in the polypeptides can be replaced by any other α-amino acid.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, (N-(lower)alkylpiperidine, and any other suitable amine.

The proteins of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of the ABI peptide synthesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky et al., *Chem. Ind. (London)* 38. 1597-98 (1966). A chloromethylated resin is commercially available from Bio Rad Laboratories, Richmond, CA and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem. Acta,* 56, 1476 (1973) Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 1-(p-biphenylyl)-1-methylethoxycarbonyl, αα-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asp or Arg is N,N′-diisopropylcarbodiimide and 1-hydroxybenzotriazole. The use of these reagents prevents nitrile and lactam formation. Other coupling agents are (1) carbodiimides (e.g., N,N′-dicyclohexylcarbodiimide and N-ethyl-N′-(γ-dimethylaminopropylcarbodiimide); (2) cyanamides (e.g., N,N dibenzylcyanamide); (3) ketenimines; (4) isoxazolium salts (e.g., N-ethyl-5-phenyl isoxazolium-3′sulfonate; (5) monocyclic nitrogen containing heterocyclic amides of aromatic character containing one through four nitrogens in the ring such as imidazolides, pyrazolides and 1,2,4-triazolides. Specific heterocyclic amides that are useful include N,N′-carbonyldiimidazole and N,N′-carbonyldi-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g. Boc-Arg-O-Arg-Boc) and (8) nitrogen containing heterocyclic compounds having a hydroxy group on one ring nitrogen (e.g., N-hydroxysuccinimide and 1-hydroxybenzotriazole). Other activating reagents and their use in peptide coupling are described by Kapoor, *J. Pharm. Sci.,* 59, pp 1–27 (1970). Applicant prefers the use of the symmetrical anhydride as a coupling reagent.

Each protected amino acid or amino acid sequence is introduced into the solid phase reactor in about a fourfold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as describe by E. Kaiser et al., *Analyt. Biochem.* 34, 595 (1970).

After the desired amino acid sequence has been obtained, the peptide is removed from the resin. This can be done by methanolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl said substituent being selected from halo (e.g. chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups are removed by procedures well known in the art. Typically protecting group removal is done after the peptide chain synthesis is complete but the protecting groups can be removed at any other appropriate time.

The polypeptide-phospholipid complexes can be prepared in a variety of ways for example by those procedures currently used by those skilled in the art to form complexes of protein isolated from alveolar lung washes and phospholipids and be accomplished by, for example, simply mixing the polypeptide and phospholipid in solution. Alternatively the complexes can be prepared by dissolving sufficient quantity of the polypeptide in 50 mm Tris-HCl having a pH=8.0 and containing 6M quanidine hydrochloride to give a polypeptide concentration of 5 mg/ml. After a 4 hour incubation at 37° C., the protein is dialyzed against a solution of 10 mm Tris-HCl having a ph=8.0 for an additional 4 hours. The polypeptide solution is then added to an approximately equal weight of dry lipid and the mixture incubated for 12 hours at 42° C. The resulting complex is isolated by density gradient ultracentrifugation and collected by, for example, dialyzing against physiological saline. Protein concentration in the isolated complexes is determined by amino acid analysis, lipid concentration by phosphorus analysis. The ratio of polypeptide to phospholipid in the complexes of this invention can be from about 1 to about 10, although any ratio which provides a complex which is effective in the treatment of RDS can be used.

The polypeptide-phospholipid complexes of this invention can be used in the treatment of neonatal respiratory distress syndrome, a physiological condition which results from the inability of the lungs of premature infants to produce pulmonary surfactant. The complexes of this invention when administered to RDS patients, act as synthetic pulmonary surfactants and either replace the natural, missing surfactant or augment the lack of sufficient natural surfactant. Treatment is continued until the infant's lungs produce a sufficient amount of natural, pulmonary surfactant so as to render further treatment unnecessary.

The complexes are administered directly to the lungs of the patient by intratracheal administration of the complex in for example, a sterile saline solution or by aerosolization and insufflation into the lungs through a tracheostomy or through the mouth and nose. The amount of complex administered will vary with the patient, the severity of the RDS, the amount of endogenous surfactant present, and the potency of the chosen complex. An effective dose will require sufficient quantity of complex to provide from about 0.1 to 50 mol of phospholipid per kg of the patient's body weight.

The relative effectiveness and potency of the polypeptide-phospholipid complexes of this invention can be readily determined by, for example, experimental trial of a complex in an animal failing lung model. The use of the failing lung model is well known to those skilled in the art and, typically, is performed by terminating the pregnancy of an animal of the test species, typically sheep, rabbits or cows, prior to full term and at a time when the fetus is known to be surfactant deficient. For example, lambs at 120–124 days gestation are surfactant deficient. Such early born animals suffer from RDS. The ability of test compound to eliminate or reduce symptoms of RDS is a measure of the efficacy and potency of the compound.

This invention is illustrated in the following, non-limiting examples.

EXAMPLE 1

Preparation of
H-Gly-Leu-Pro-Ala-His-Leu-Asp-Glu-Glu-Leu-Gln-Ala-Thr-Leu-His-Asp-Phe-Arq-His-Gln-Ile-Leu-Gln-Thr-OH Three grams of benzylated methoxyphenylacetamidomethyl resin (PAM) bound Boc-Thr is placed in the reaction vessel of a peptide synthesizer and the synthesis accomplished by treating the resin in the following manner:

Protocol for Solid Phase Peptide Synthesis

| STEP | FUNCTION | PROCEDURE |
|---|---|---|
| 1 | Washing | $CH_2Cl_2$ (three times) |
| 2 | Deblocking | 2 minute prewash with 1:1 TFA-$CH_2Cl_2$ followed by a 28 minute wash with the same TFA-$CH_2Cl_2$ mixture |
| 3 | Washing | $CH_2Cl_2$ (five times) |
| 4 | Neutralization | 5% DIPEA in $CH_2Cl_2$ (three times) |
| 5 | Washing | $CH_2Cl_2$ (four times) |
| 6 | Coupling | 4 equivalents of Boc protected symmetrical anhydride the appropriate amino acid for 2 hours (4 equivalent of Boc-Gln, Boc-Asp or Boc-Arg(Tos) with DCC and HBT where Gln, Asp or Arg is the amino acid to be coupled) |
| 7 | Washing | $CH_2Cl_2$ (four times) |
| 8 | Neutralization | 5% DIPEA in $CH_2Cl_2$ |
| 9 | Washing | $CH_2Cl_2$ (four times) |
| 10 | Coupling Repeat | 4 equivalents of the Boc protected HBT ester of the appropriate amino acid for 2 hours |
| 11 | Washing | DMF (two times), $CH_2Cl_2$ (two times) |
| 12 | Neutralization | 5% DIPEA in $CH_2Cl_2$ |
| 13 | Washing | $CH_2Cl_2$ (four times) |
| 14 | Monitoring | Qualitative Ninhydrin Test |

Boc, t-butyloxycarbonyl; DCC, dicyclohexylcarbodiimide; DIPEA, diisopropylethylamine; DMF, dimethylformamide; HBT, 1-hydroxybenzotriazole; TFA, trifluoroacetic acid.

After the amino terminal Gly residue is added, the resin is first treated with 5 ml of aqueous HF containing 65% dimethyl sulfide, 7.5% p-cresol and 2.5% thiocresol for 2 hours at 0° C. and then with 5 ml of aqueous HF containing 7.5% p-cresol and 2.5% p-thiocresol for 1 hour at 0° C. to remove the polypeptide from the resin and remove any blocking groups.

The polypeptide is purified by dissolving in 1M Tris-6M guanidine-HCl, pH 8.0, and subjected to chromatography on a Sephadex G-25 column (2.5×100 cm) equilibrated with 0.1M Tris-HCl, 6M urea, pH 8.1. Further purification of the peptides is carried out by preparative high performance liquid chromatography with a Beckman Ultrapore RPSC C-3 column (4.6×75 mm; particle size 5 μm; pore size 30 nm). The peptide is dissolved in 6M guanidine-HCl in 1% triethylammonium phosphate, pH 6.75, loaded onto the C-3 column and eluted with a linear gradient of 0–50% acetonitrile in 1% triethylammonium phosphate, pH 6.75. Peptides are collected and desalted on a Sep-pak C-18 cartridge (Waters Associates) and lyophilized. Peptide concentrations are determined by amino acid analysis. Criteria of purity include: (1) analytical HPLC; (2) amino acid sequence determination; and (3) elemental analysis.

EXAMPLE 2

Preparation of the DPPC complex of the Polypeptide of Example 1

The lipid-binding polypeptide of Example 1 is dissolved in 50 mM Tris-HCl, pH 8.0, containing 6M guanidine-HCl to give a final peptide concentration of 5 mg/ml, and then incubated at 37° C. for 4 hours; the peptide is then dialyzed for 4 hours against 10 mM Tris-HCl, pH 8.0. DPPC (5 mg) is dissolved in 1 ml $CHCl_3$, evaporated to dryness with a stream of pure nitrogen, and dried under vacuum for 1 hour. One ml of the peptide solution is then added to the dry lipid and the mixture is incubated at 42° C. for 12 hours. The polypeptide-phospholipid complex is isolated by density gradient ultracentrifugation. A linear gradient of KBr (d, 1.006–1.37 g/ml) is prepared with a gradient former. The polypeptide-phospholipid complex is dissolved in 10 mM Tris-HCl, 150 mM NaCl, pH 8.0, and mixed with an equal volume of KBr (d-1.37 g/ml) in 10 mM Tris-HCl, pH 8.0. After centrifugation for 20 hours at 15° C. and 38,000 rpm in a Beckman SW 41 rotor, fractions are obtained by puncturing the tube and collecting 0.6-ml fractions. The complex is collected, dialyzed against physiological saline, and sterile-filtered. Peptide concentration in the isolated complex is determined by amino acid analysis; lipid concentration is measured by phosphorous analysis.

EXAMPLE 3

An illustrative composition for an intratracheal solution is as follows:

| Complex of Example 2 | 3.75 g |
|---|---|
| Sodium chloride | 90 g |
| Distilled water quantum sufficient | 10 l |

The former two reagents are dissolved in the water, then filtered under sterile conditions.

I claim:

1. A polypeptide of the formula

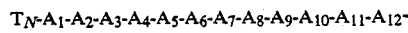

wherein
$A_1$, $A_4$, $A_5$, $A_8$, $A_9$, $A_{11}$, $A_{12}$, $A_{15}$, $A_{16}$, $A_{18}$, $A_{19}$ and $A_{20}$ are each independently selected from Gln, Glu, Asp, His, Arg, Lys, Ser, Ala, Gly, Tyr, Typ, and Thr;
$A_2$ is Leu, Gln, Glu, Asp, His, Arg, Lys, Ser, Ala, Gly, Thr, Typ or Thr;
$A_3$ is Pro, Ile, Val, Phe, Met, Ala, Gly, Tyr, Typ or Thr;
$A_6$, $A_7$, $A_{13}$ and $A_{14}$ are each independently selected from Leu, Ile, Val, Phe, Met, Gln, Glu, Asp, His, Arg, Lys, Ser, Ala, Gly, Tyr, Typ and Thr;
$A_{10}$, $A_{17}$ and $A_{21}$ are each independently selected from Leu, Ile, Val, Phe, Met, Gln, Glu, Asp, His, Arg, Lys, Ser, Ala, Gly, Tyr, Typ, and Thr;
$T_n$ is
$T_{N'}$-Arg-Gly-Pro-Pro-,
$T_{N'}$-Gly-Pro-Pro-,
$T_{N'}$-Pro-Pro-,
$T_{N'}$-Pro-, or
$T_{N'}$-;
$T_C$ is
-Leu-Gln-Thr-Arg-Gly-$T_{C'}$,
-Leu-Gln-Thr-Arg-$T_{C'}$,
-Leu-Gln-Thr-$T_{C'}$,
-Leu-Gln-$T_{C'}$,
-Leu-$T_{C'}$, or
-$T_{C'}$;
$T_{N'}$ is hydrogen, an amino acid, dipeptide, or tripeptide, or an aliphatic, aromatic or cyclic organic acid having 1 to 10 carbon atoms; and
$T_{C'}$ is hydrogen, a ($C_1$–$C_6$) alkyl, or benzyl, optionally substituted with one or two members of the group consisting of nitro, methyl and methoxy, or $T_{C'}$ phenacyl, phthalimidomethyl, benzhydryl, trichloroethyl, 4-picolyl, $\beta$-methylthioethyl or 4(methylthio)phenyl or a pharmaceutically acceptable salt thereof.

2. A polypeptide of claim 1 wherein
$A_5$ and $A_{15}$ are each His,
$A_6$, $A_{10}$ and $A_{14}$ are each Leu,
$A_7$ and $A_{16}$ are each Asp,
$A_8$ and $A_9$ are each Glu,
$A_{11}$ is Gln,
$A_{12}$ is Ala,
$A_{13}$ is Thr, and
$A_{17}$ is Phe.

3. A polypeptide of claim 1 wherein $A_7$ is Asp or Leu.

4. A polypeptide of claim 1 wherein $A_{13}$ is Thr or Leu.

5. A polypeptide of claim 1 wherein $A_6$, $A_{10}$ and $A_{14}$ are Leu an $A_{17}$ is Phe.

6. A polypeptide of claim 1 having the formula

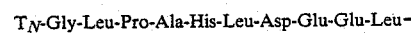

7. A polypeptide of claim 6 wherein $T_C$ is -Leu-Gln-Thr-$T_{C'}$.

8. A polypeptide-phospholipid complex comprising a polypeptide of claim 1 and a phospholipid selected from a phosphoglyceride or a sphingolipid.

9. A polypeptide-phospholipid complex of claim 8 wherein
$A_5$ and $A_{15}$ are each His,
$A_6$, $A_{10}$ and $A_{14}$ are each Leu,
$A_7$ and $A_{16}$
are each Asp,
$A_8$ and $A_9$ are each Glu,
$A_{11}$ is Gln,
$A_{12}$ is Ala,
$A_{13}$ is Thr, and
$A_{17}$ is Phe.

10. A polypeptide-phospholipid complex of claim 8 wherein $A_7$ is Asp or Leu.

11. A polypeptide-phospholipid complex of claim 8 wherein $A_{13}$ is Thr or Leu.

12. A polypeptide-phospholipid complex of claim 8 wherein $A_6$, $A_{10}$, and $A_{14}$ are Leu and $A_{17}$ is Phe.

13. A polypeptide-phospholipid complex of claim 8 wherein the polypeptide has the formula $T_N$-Gly-Leu-Pro-Ala-His-Leu-Asp-Glu-Glu-Leu⌐

└─Gln-Ala-Thr-Leu-His-Asp-Phe-Arg-His-Gln-Ile-$T_C$

14. A polypeptide-phospholipid complex of claim 13 wherein $T_C$ is -Leu-Gln-Thr-$T_{C'}$.

15. A polypeptide-phospholipid complex of one of claims 8–14 wherein the phospholipid is dipalmitoylphosphatidylcholine.

16. A method of treating neonatal respiratory distress syndrome which comprises administering to a patient in need thereof an effective amount of a polypeptide-phospholipid complex of claim 8.

17. A method of claim 16 wherein
$A_5$ and $A_{15}$ are each His,
$A_6$, $A_{10}$ and $A_{14}$ are each Leu,
$A_7$ and $A_{16}$ are each Asp,
$A_8$ and $A_9$ are each Glu,
$A_{11}$ is Gln,
$A_{12}$ is Ala,
$A_{13}$ is Thr, and
$A_{17}$ is Phe.

18. A method of claim 16 wherein $A_7$ is Asp or Leu.

19. A method of claim 16 wherein $A_{13}$ is Thr or Leu.

20. A method of claim 16 wherein $A_6$, $A_{10}$, and are Leu and $A_{17}$ is Phe.

21. A method of claim 16 wherein the polypeptide has the formula $T_N$-Gly-Leu-Pro-Ala-His-Leu-Asp-Glu-Glu-Leu⌐

└─Gln-Ala-Thr-Leu-His-Asp-Phe-Arg-His-Gln-Ile-$T_C$

22. A method of claim 21 wherein T is -Leu-Gln-Thr-$T_{C'}$.

23. A method of any of claims 16–22 wherein the phospholipid is dipalmitoylphosphatidylcholine.

* * * * *

UNITED STATES PATENT AND TRADEMARK OFFICE
CERTIFICATE OF CORRECTION

PATENT NO. : 4,861,756  
DATED : August 29, 1989  
INVENTOR(S) : Richard L. Jackson It is certified that error appears in the above-identified patent and that said Letters Patent is hereby corrected as shown below:

Column 2, line 33, the patent reads "L-$T_c$';" and should read --$T_c$'; --

Column 4, line 21, the patent reads "other t glycine" and should read --other than glycine --

Column 6, line 11, the patent reads "(e.g., N-hydroxysuccinimide" and should read --(e.g. N-hydroxyphthalimide, N-hydroxysuccinimide --

Column 5, line 15, the patent reads "as an coupling" and should read --as a coupling --.

Column 6, line 28, the patent reads "as describe" and should read --as described--

Column 10, claim 5, line 35, the patent reads "are Leu an $A_{17}$" and should read --are Leu and $A_{17}$--

Column 12, claim 20, line 7, the patent reads "$A_{10}$, and are" and should read --$A_{10}$', and $A_{14}$ are --

UNITED STATES PATENT AND TRADEMARK OFFICE
CERTIFICATE OF CORRECTION

PATENT NO. : 4,861,756

DATED : August 29, 1989

INVENTOR(S) : Richard L. Jackson

It is certified that error appears in the above-identified patent and that said Letters Patent is hereby corrected as shown below:

Column 12, claim 22, line 18, the patent reads "wherein T" and should read --wherein $T_c$ --

Signed and Sealed this

Twentieth Day of November, 1990

Attest:

HARRY F. MANBECK, JR.

Attesting Officer

Commissioner of Patents and Trademarks